United States Patent [19]
Yoon

[11] Patent Number: 5,569,289
[45] Date of Patent: *Oct. 29, 1996

[54] SAFETY PENETRATING INSTRUMENT WITH PENETRATING MEMBER AND CANNULA MOVING DURING PENETRATION AND TRIGGERED SAFETY MEMBER PROTUSION

[76] Inventor: InBae Yoon, 2101 Highland Ridge Dr., Phoenix, Md. 21131

[ * ] Notice: The term of this patent shall not extend beyond the expiration date of Pat. No. 5,431,635.

[21] Appl. No.: 317,939

[22] Filed: Oct. 4, 1994

Related U.S. Application Data

[63] Continuation-in-part of Ser. No. 83,220, Jun. 24, 1993, Pat. No. 5,431,635, Ser. No. 83,728, Jun. 29, 1993, Pat. No. 5,466,224, and Ser. No. 115,152, Sep. 2, 1993.

[51] Int. Cl.$^6$ .................................. A61M 5/20
[52] U.S. Cl. ..................... 606/185; 604/165; 604/170
[58] Field of Search .................................. 128/751, 752, 128/753, 754; 604/95, 158, 162, 163, 164, 165, 170, 272, 274, 280, 169; 606/167, 171, 185

[56] References Cited

U.S. PATENT DOCUMENTS

| | | |
|---|---|---|
| 1,087,845 | 2/1914 | Stevens . |
| 1,213,001 | 1/1917 | Philips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,828,547 | 5/1989 | Sahi et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |
| 5,030,206 | 7/1991 | Lander . |
| 5,053,016 | 10/1991 | Lander . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9304632 | 3/1993 | WIPO . |
| 9304715 | 3/1993 | WIPO . |
| 9304716 | 3/1993 | WIPO . |
| 9317626 | 9/1993 | WIPO . |

*Primary Examiner*—Guy V. Tucker

[57] ABSTRACT

A safety penetrating instrument includes a penetrating member, a safety member movable between an extended position where the safety member distal end protrudes distally of the penetrating member distal end and a retracted position where the safety member distal end is disposed proximally of the penetrating member distal end, an extending mechanism for moving the safety member distally from the retracted position to the extended position, a handle for manually moving the safety member proximally from the extended position to the retracted position and a lock for locking the safety member in the retracted position. A releasing mechanism responsive to distally-biased movement of the safety member and/or the penetrating member upon penetration into the anatomical cavity triggers release of the lock to permit the extending mechanism to move the safety member to the extended position.

29 Claims, 10 Drawing Sheets

U.S. PATENT DOCUMENTS

| | | |
|---|---|---|
| 5,127,909 | 7/1992 | Shichman . |
| 5,152,754 | 10/1992 | Plyley et al. . |
| 5,158,552 | 10/1992 | Borgia et al. . |
| 5,207,647 | 5/1993 | Phelps . |
| 5,215,526 | 6/1993 | Deniega et al. . |
| 5,224,951 | 7/1993 | Freitas . |
| 5,224,952 | 7/1993 | Deniega et al. . |
| 5,226,426 | 7/1993 | Yoon . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,290,243 | 3/1994 | Chodorow et al. . |
| 5,290,304 | 3/1994 | Storace . |
| 5,295,993 | 3/1994 | Green . |
| 5,312,354 | 3/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen . |
| 5,350,393 | 9/1994 | Yoon . |
| 5,360,405 | 11/1994 | Yoon . |
| 5,364,372 | 11/1994 | Danks et al. . |
| 5,366,445 | 11/1994 | Haber et al. . |
| 5,368,607 | 11/1994 | Freitas . |
| 5,372,588 | 12/1994 | Farley et al. . |
| 5,374,252 | 12/1994 | Banks et al. . |
| 5,376,082 | 12/1994 | Phelps . |
| 5,380,288 | 1/1995 | Hart et al. . |
| 5,383,859 | 1/1995 | Sewell, Jr. . |
| 5,431,635 | 7/1995 | Yoon ........................................ 604/165 |

FIG. I

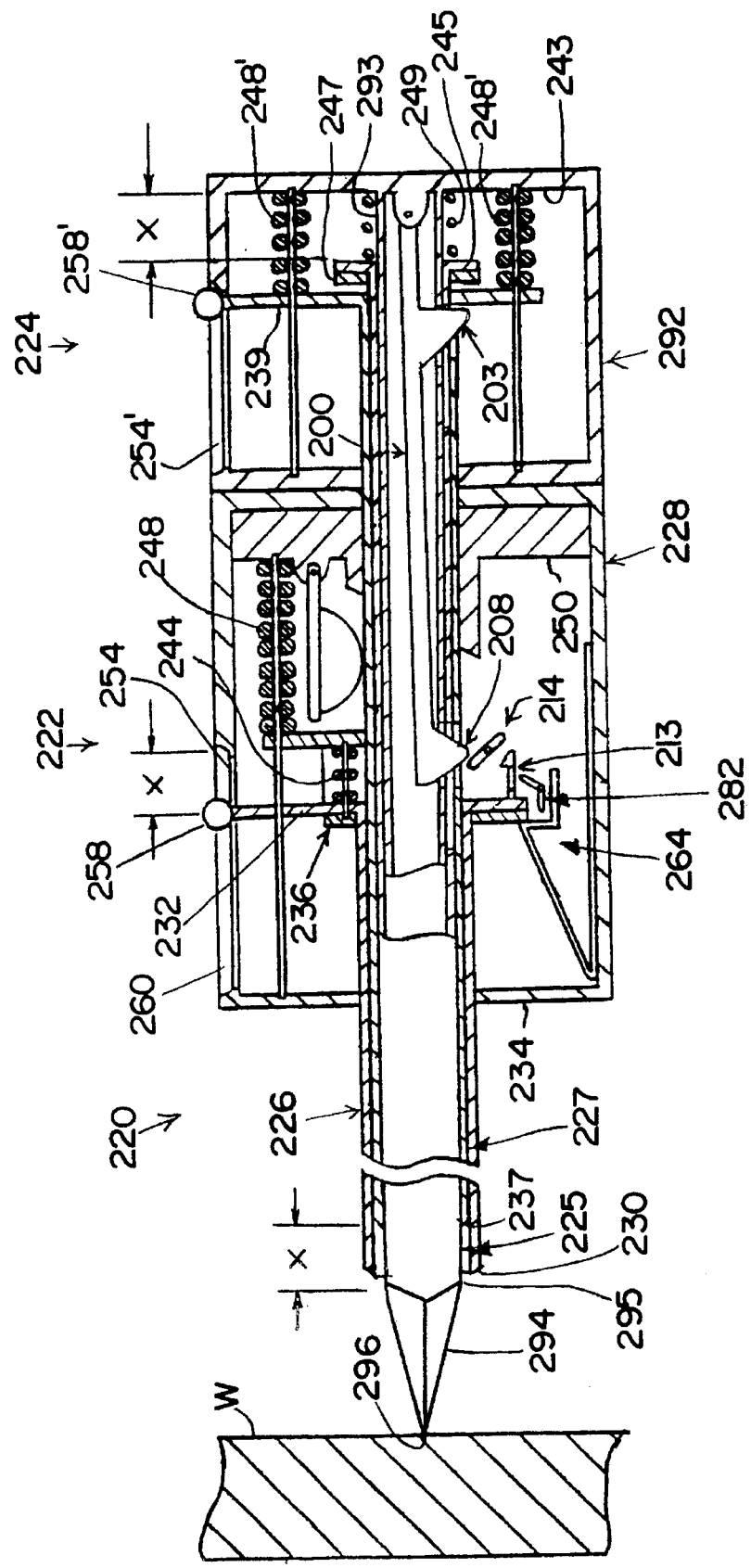
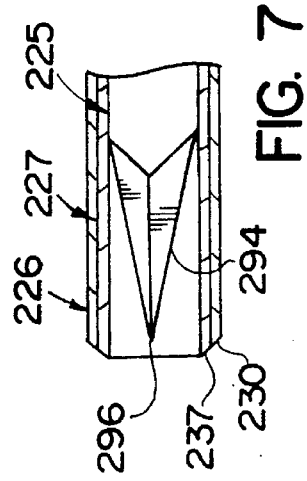
FIG. 6
FIG. 7

SAFETY PENETRATING INSTRUMENT WITH PENETRATING MEMBER AND CANNULA MOVING DURING PENETRATION AND TRIGGERED SAFETY MEMBER PROTUSION

CROSS-REFERENCE TO RELATED APPLICATIONS

This application is a continuation-in-part of prior applications Ser. No. 08/083,220, filed Jun. 24, 1993, now U.S. Pat. No. 5,431,635, Ser. No. 08/083,728, filed Jun. 29, 1993, now U.S. Pat. No. 5,466,224, and Ser. No. 08/115,152, filed Sep. 2, 1993, still pending, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to improve safety penetrating instruments of the type having a penetrating member and a safety member biased distally to protrude beyond the distal end of the penetrating member by easing penetration and assuring protrusion of the safety member.

Another object of the present invention is to reduce the force-to-penetrate required to penetrate an anatomical cavity wall with a safety penetrating instrument of the type having a distally biased safety member for protruding beyond a distal end of a penetrating member once penetration into the cavity has been achieved.

A further object of the present invention is to increase the force biasing a safety member distally in a safety penetrating instrument to assure protrusion of the safety member after penetration into an anatomical cavity without increasing the force-to-penetrate required for penetration.

The present invention has an additional object to permit proximal movement of the cannula and penetrating member of a safety penetrating instrument during penetration of an anatomical cavity wall and to utilize the cannula as a safety member triggered to move distally from a retracted position exposing the distal end of the penetrating member to an extended protruding position covering the penetrating member distal end in response to distally-biased movement of the cannula upon entering the anatomical cavity.

Another object of the present invention is to permit proximal movement of the cannula and penetrating member of a safety penetrating instrument during penetration of an anatomical cavity wall and to utilize the safety shield or probe as a safety member triggered to move distally from a retracted position exposing the distal end of the penetrating member to an extended protruding position covering the penetrating member distal end in response to distally-biased movement of the cannula upon entering the anatomical cavity.

Yet another object of the present invention is to permit proximal movement of the cannula and penetrating member of a safety penetrating instrument during penetration of an anatomical cavity wall and to utilize the cannula and safety shield or probe as safety members triggered to move distally from retracted positions exposing the distal end of the penetrating member to extended protruding positions covering the penetrating member distal end in response to distally-biased movement of the cannula upon entering the anatomical cavity.

An additional object of the present invention is to permit proximal movement of the cannula and penetrating member of a safety penetrating instrument during penetration of an anatomical cavity wall and to utilize the cannula as a safety member triggered to move distally from a retracted position exposing the distal end of the penetrating member to an extended protruding position covering the penetrating member distal end in response to distally-biased movement of the penetrating member upon entering the anatomical cavity.

Still another object of the present invention is to permit proximal movement of the cannula and penetrating member of a safety penetrating instrument during penetration of an anatomical cavity wall and to utilize the cannula as a safety member triggered to move distally from a retracted position exposing the distal end of the penetrating member to an extended protruding position covering the penetrating member distal end in response to distally-biased movement of both the cannula and penetrating member upon entering the anatomical cavity.

Yet a further object of the present invention is to permit proximal movement of the cannula and penetrating member of a safety penetrating instrument during penetration of an anatomical cavity wall and to utilize the safety shield or probe as a safety member triggered to move distally from a retracted position exposing the distal end of the penetrating member to an extended protruding position covering the penetrating member distal end in response to distally-biased movement of the penetrating member upon entering the anatomical cavity.

A further object of the present invention is to permit proximal movement of the cannula and penetrating member of a safety penetrating instrument during penetration of an anatomical cavity wall and to utilize the safety shield or probe as a safety member triggered to move distally from a retracted position exposing the distal end of the penetrating member to extended protruding positions covering the penetrating member distal end in response to distally-biased movement of the cannula and penetrating member upon entering the anatomical cavity.

It is also an object of the present invention to permit proximal movement of the cannula and penetrating member of a safety penetrating instrument during penetration of an anatomical cavity wall and to utilize both the cannula and safety shield or probe as safety members triggered to move distally from retracted positions exposing the distal end of the penetrating member to extended protruding positions covering the penetrating member distal end in response to distally-biased movement of the penetrating member upon entering the anatomical cavity.

An additional object of the present invention is to permit proximal movement of the cannula and penetrating member of a safety penetrating instrument during penetration of an anatomical cavity wall and to utilize both the cannula and safety shield or probe as safety members triggered to move distally from retracted positions exposing the distal end of the penetrating member to extended protruding positions covering the penetrating member distal end in response to distally-biased movement of both the cannula and penetrating member upon entering the anatomical cavity.

Some of the advantages of the safety penetrating instrument of the present invention are that the distal extending force on a safety member can be designed to assure protrusion of the safety member upon penetration regardless of the anatomical cavity being penetrated, that the force-to-penetrate of a safety penetrating instrument can be minimized to permit use in delicate tissue, that release of the safety member for movement to the extended protruding position can be triggered by distally biased movement of a cannula and/or a penetrating member in response to penetration of the instrument through the tissue, and that the safety penetrating instrument can be inexpensively manufactured with minimum components to reduce cost, facilitate sterilization for re-use and allow economical single-patient use.

The present invention is generally characterized in a safety penetrating instrument including a penetrating member having a distal end for penetrating an anatomical cavity wall to gain access to an anatomical cavity, a safety member having a distal end movable between an extended position where the safety member distal end is disposed distally of the penetrating member distal end to protect the penetrating member distal end and a retracted position where the safety member distal end is disposed proximally of the penetrating member distal end to expose the penetrating member distal end, extending means for moving the safety member distally to the extended position and for permitting the safety member to move proximally to the retracted position, means for manually moving the safety member proximally from the extended position to the retracted position and locking means for locking the safety member in the retracted position to prevent movement of the safety member to the extended position during penetration of the anatomical cavity wall. The safety member can be a safety shield or probe and/or a cannula biased distally in the retracted position to be movable proximally from the retracted position during penetration of the anatomical cavity wall by the safety penetrating instrument and distally toward the retracted position upon penetration into the anatomical cavity by the safety penetrating instrument. Releasing means responsive to distally-biased movement of the cannula and/or the penetrating member upon penetration into the anatomical cavity triggers release of the locking means to permit the extending means to move the safety member to the extended position.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

BRIEF DESCRIPTION OF THE DRAWINGS

FIG. 6 is a broken side view, partly in section, of another modification of the safety penetrating instrument according to the present invention.

FIG. 7 is a side view, partly in section, of the distal end of the safety penetrating instrument of FIG. 6 following penetration into the anatomical cavity.

DESCRIPTION OF THE PREFERRED EMBODIMENTS

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
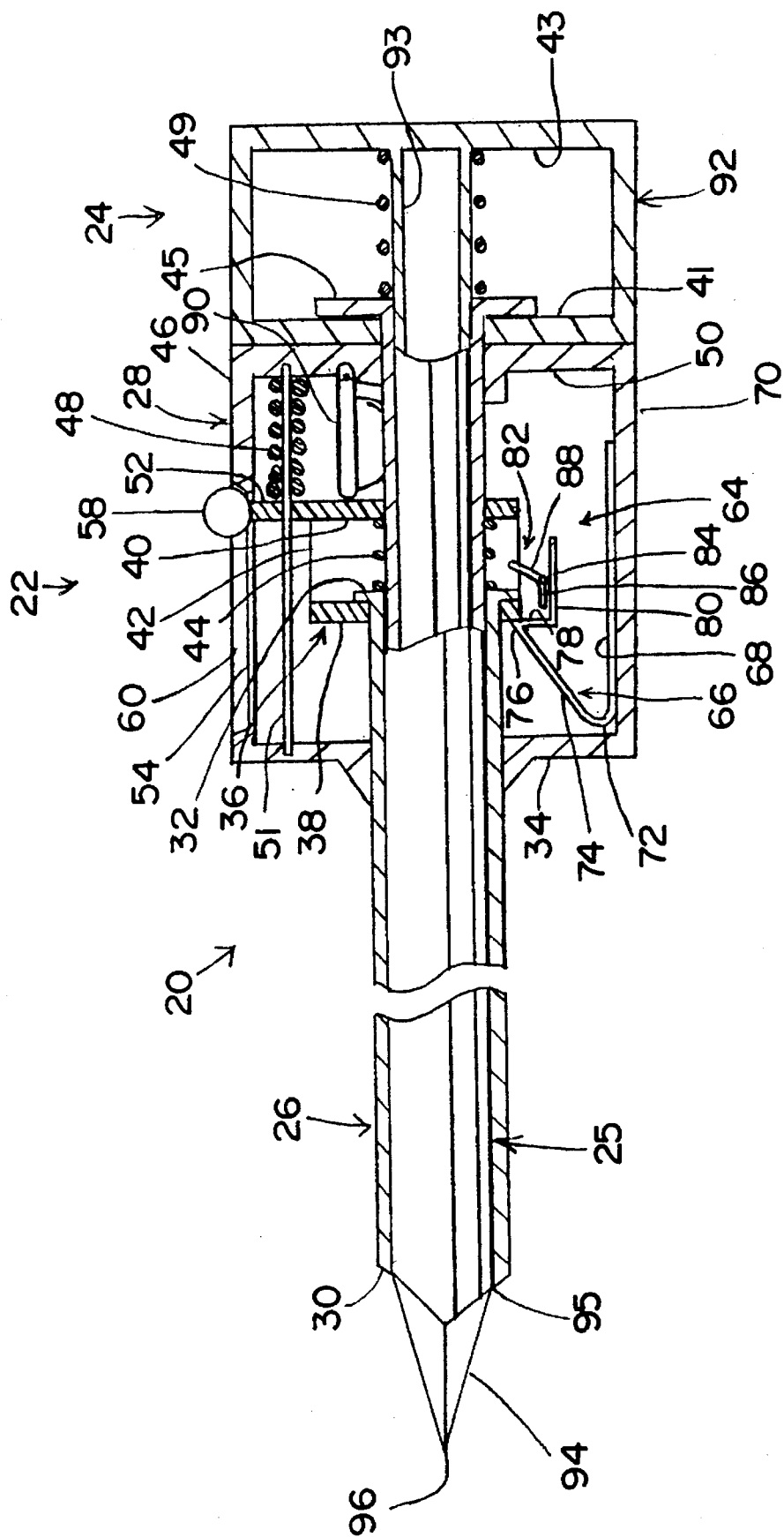
FIG. 1 is a broken side view, partly in section, of a safety penetrating instrument according to the present invention.

A safety penetrating instrument 20 according to the present invention, as shown in FIG. 1, is formed of a portal unit 22 and a penetrating unit 24. The portal unit 22 can be made of any desirable, medical grade materials depending on procedural use and desirability of being for single patient use or re-usable. The portal unit 22 includes an elongate portal sleeve, cannula or catheter 26 and a housing 28 mounting a proximal end of portal sleeve 26. Portal sleeve 26 terminates distally at a distal end 30 and proximally at a transverse flange 32 disposed in housing 28 with the portal sleeve passing through an opening in a front wall 34 of the housing. Portal sleeve 26 can have any desirable cross-sectional configuration, including cylindrical or tubular configurations, in accordance with the procedure to be performed and the anatomical cavity to be penetrated. Preferably, the portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 25 of penetrating unit 24.

A rail member 36 is disposed in housing 28 and is generally U-shaped including a forward wall 38 disposed transverse or perpendicular to a longitudinal axis of the penetrating instrument, a rearward wall 40 in configuration parallel to forward wall 38 and a side wall 42 transversely joining the forward and rearward rail member walls. Flange 32 is disposed between the rail member forward and rearward walls with the rail member forward wall 38 having an opening therein allowing passage therethrough by the portal sleeve 26. The rail member forward and rearward walls are disposed parallel or substantially parallel to flange 32, and a bias member 44 is connected between flange 32 and the rail member rearward wall 40 to bias the portal sleeve distally. As shown, bias member 44 includes a helical coil spring 44 disposed around the penetrating member 25 and mounted in compression between flange 32 and the rail member rearward wall 40 to bias the portal sleeve 26 distally to cause flange 32 to abut the rail member forward wall 38. However, bias member 44 can include various other types of springs as well as other types of bias devices including compression springs, tension springs, torsion springs, pan springs, leaf springs, rubber, plastic or magnets, for example. Rail member rearward wall 40 extends toward an upper wall 46 of housing 28, and an extending member 48 is mounted between rail member rearward wall 40 and a rear wall 50 of housing 28 to bias the portal sleeve 26 in a distal direction to an extended protruding position where a distal end 30 of the portal sleeve is positioned beyond a sharp tip of the penetrating member 25 as will be explained further below. The extending member can include a helical coil spring 48 mounted in compression between rail member rearward wall 40 and the housing rear wall 50 as shown, or the extending member can include any other type of spring or other bias devices discussed for bias member 44. If desired, a guide rod 51 can be connected between the front wall 34 and the rear wall 50 of housing 28 with the spring 48 disposed around the guide rod.

Rail member rearward wall 40 extends toward the upper wall 46 of housing 28, and a pin 52 extends from rail member rearward wall 40 through a slot 54 in the housing upper wall 46 to terminate in a handle or knob 58 positioned in an elongate, trough-like recess 60 in the housing upper wall. Slot 54 and recess 60 extend longitudinally in parallel with the longitudinal axis of the safety penetrating instrument 20.

A locking and releasing mechanism 64 for locking the portal sleeve in a retracted position, shown in FIG. 1, exposing the sharp distal end of the penetrating member and for releasing the portal sleeve to allow the portal sleeve to move to the extended protruding position includes a latch or locking spring 66, made of a strip of resilient material, formed to have a substantially flat base 68 secured to a bottom wall 70 of housing 28 and a bend 72 joining the base 68 with an upwardly angled arm 74 spaced from the base. Arm 74 carries or forms a latch 76 having a distal angled latching surface joining a proximal latching surface 78 disposed substantially transverse to the longitudinal axis of the safety penetrating instrument and substantially parallel to the rail member forward wall 38. Arm 74 has an extension 80 positioned proximally of latch 76, and a releasing member or trigger 82 is juxtaposed with extension 80. The trigger 82 is pivotally mounted in the housing on a pin 84 secured to a wall or walls of the housing or structure supported in the housing, and the trigger is generally L-shaped with a leg 86 overlying extension 80 and a leg 88 extending transversely from leg 86 but at a slight angle toward the proximal end of the safety penetrating instrument. A torsion spring (not shown) is coiled around pin 84 and fixed to trigger 82 to bias the trigger counterclockwise, looking at FIG. 1, such that leg 86 is biased toward extension 80.

The portal sleeve distal end 30 can have various configurations to protect tissue within an anatomical cavity by covering the distal tip of the penetrating member in the extended protruding position; and, as shown, the portal sleeve distal end defines an annular or peripheral edge having a chamfered configuration to protect tissue within the anatomical cavity.

The housing 28 can be made of any desirable material and can have any desirable configuration to facilitate grasping by the user and includes a rear wall having an opening therein aligned with the opening in the housing front wall to allow passage therethrough by the penetrating member. The housing 28 is preferably constructed to sealingly engage instruments passing therethrough and to include a valve 90 biased to a closed state when no instrument passes through the portal sleeve. A flapper valve is shown; however, any suitable valve construction can be utilized, for example, trumpet or nipple valves.

The penetrating unit 24 includes penetrating member 25, a hub 92 and a guide tube 93 extending distally from a rear wall 43 of the hub. Penetrating member 25 has an elongate shaft or body which is at least partly hollow to be telescopically fitted over guide tube 93. The penetrating member terminates proximally at a transverse flange 45 and has a tapered distal end 94 extending from a transverse dimensional transition 95 in the shaft or body and terminating at a distal tip 96.

A bias member 49 is connected between the penetrating member flange 45 and the hub rear wall 43 to bias the penetrating member distally. As shown, bias member 49 includes a helical coil spring disposed around guide tube 93 and mounted in compression between penetrating member flange 45 and hub rear wall 43. The penetrating member distal end 94 can have any configuration desired by the user for a particular procedure, for example, the pyramidal trocar configuration shown or conical, threaded, multi-faceted or open, slanted or needle configurations. The penetrating member 25 can be made of any suitable, medical grade materials and can be made of multiple components such that, for example, the distal end 94 is made of stainless steel and secured in a conventional manner, such as by threads, to the distal end of the shaft, which can be tubular and made of a less expensive material, such as plastic or metal. Hub 92 can be made of any desirable medical grade material and can have any desired configuration in cross-section to facilitate grasping of the hub in the housing by a user with one hand.

The portal unit 22 and the penetrating unit 24 can be provided to a user separately or assembled together as shown in FIG. 1, and either or both of the portal and penetrating units can be manufactured in a manner to be disposable for single patient use or to be sterilizable for re-use. The hub 92 can be coupled to the housing 28 by a suitable detent or latch mechanisms if desired, and the penetrating unit can be withdrawn from the portal unit leaving the portal sleeve 26 in place within an anatomical cavity.

Figure 3:
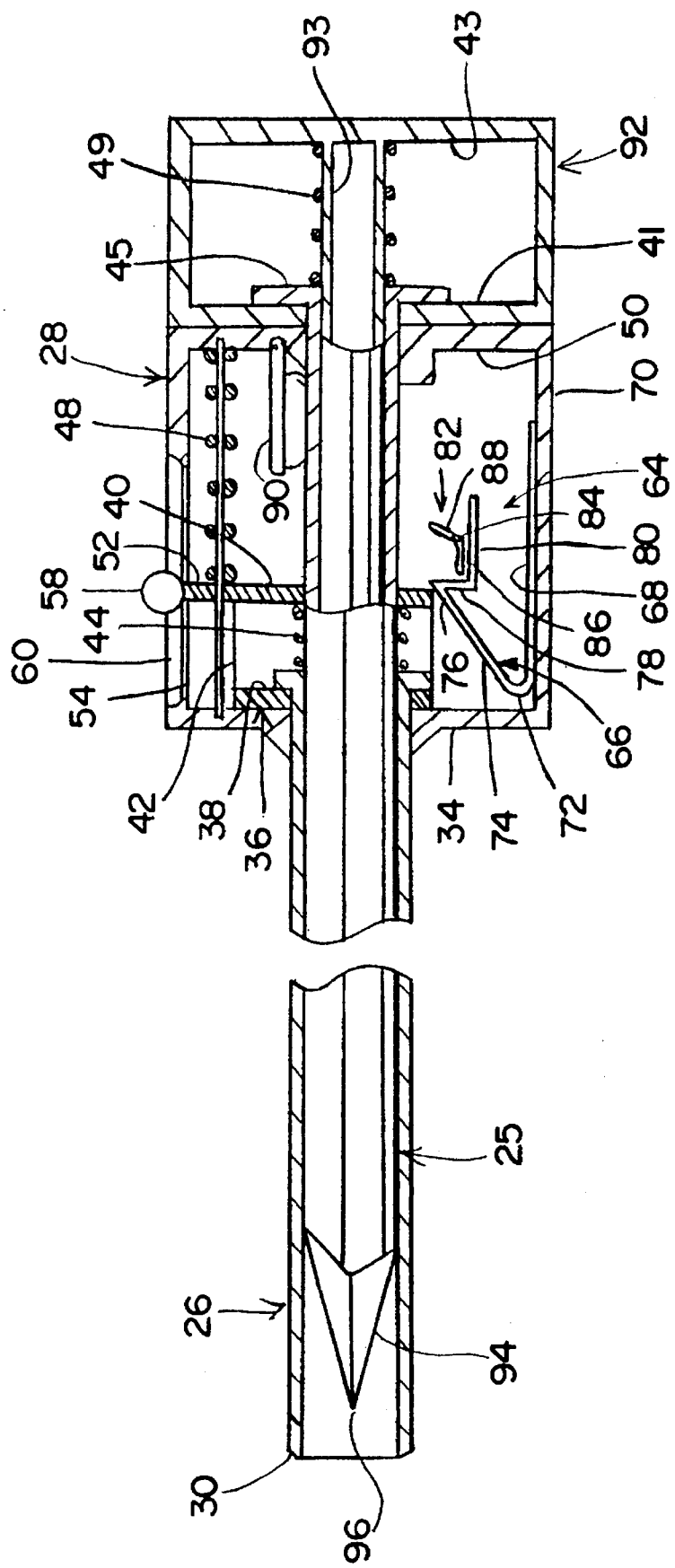
FIG. 3 is a broken side view, partly in section, of the safety penetrating instrument of FIG. 1 following penetration into the anatomical cavity.

In use, when a user desires to penetrate into an anatomical cavity using the safety penetrating instrument 20, the instrument is in the condition shown in FIG. 3 with the penetrating member 25 in a rest position where penetrating member flange 45 abuts hub front wall 41 and with portal sleeve 26 in the extended protruding position to cover the distal end 94 of the penetrating member 25. With the safety penetrating instrument 20 in the condition shown in FIG. 3, flange 32 will be in abutment with the forward wall 38 of rail member 36 due to the bias of bias member 44, and handle 58 will be disposed at a distal end of slot 54 due to the bias of extending member 48. Prior to commencing penetration of an anatomical cavity wall W, handle 58 is grasped and manually moved proximally to move the portal sleeve 26 proximally against the bias of the extending member 48 until the forward wall 38 of rail member 36 rides over latch 76 by engaging the distal latching surface to move arm 74 toward base 68. At this time, the user can feel the rail member 36 lock into place in engagement with the proximal latching surface 78 as arm 74 springs back and can also visually determine that the portal sleeve is locked in the retracted position by noting the position of handle 58.

The safety penetrating instrument 20 is now in the position illustrated in FIG. 1 with the portal sleeve 26 locked in the retracted position by locking and releasing mechanism 64 and the penetrating member 25 in the rest position with the penetrating member distal end 94 extending from the distal end of the portal sleeve. With the portal sleeve 26 locked in the retracted position and the penetrating member 25 in the rest position, portal sleeve distal end 30 will be disposed proximate penetrating member transverse dimensional transition 95 (i.e., the base of the distal end), and flange 32 will be in abutment with the forward wall 38 of rail member 36 and will be disposed distally of leg 88 of trigger 82.

Figure 2:
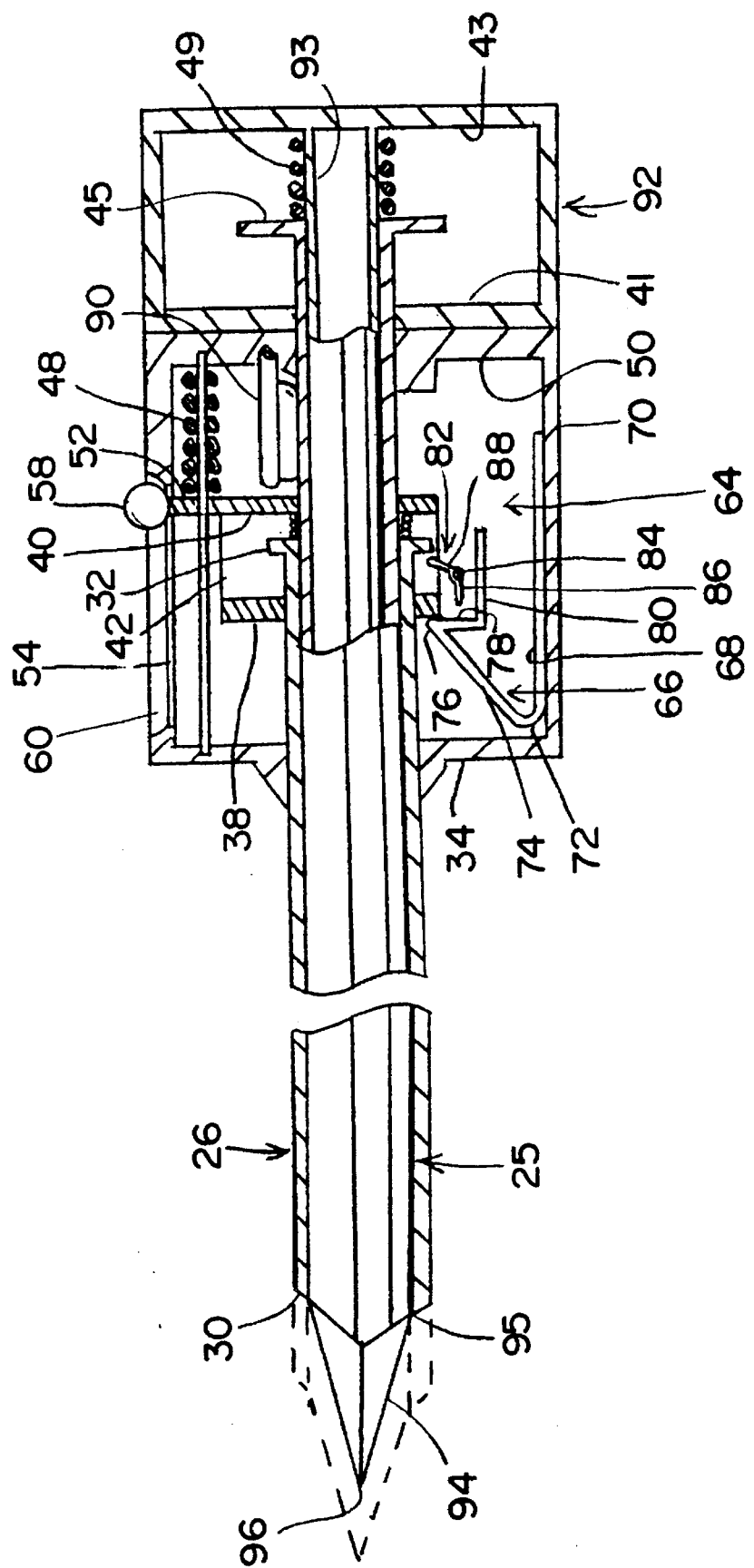
FIG. 2 is a broken side view, partly in section, of the safety penetrating instrument of FIG. 1 during penetration of a wall of an anatomical cavity.

As penetration of the anatomical cavity wall W is commenced, the force from tissue contact on the distal end 94 of the penetrating member will cause the penetrating member to move proximally within hub 92, as shown in FIG. 2, and the penetrating member distal end 94 will penetrate into the cavity wall. As penetration continues, the force from tissue contact on the distal end of the portal sleeve 26 will cause the portal sleeve to move proximally together with the penetrating member, causing the operating member formed by flange 32 to move proximally until flange 32 abuts the rearward wall 40 of rail member 36 which serves as a stop or abutment limiting proximal movement of the portal sleeve. Proximal movement of the penetrating member 25 is similarly limited by abutment of the penetrating member flange 45 with hub rear wall 43. Since both the portal sleeve 26 and penetrating member 25 move proximally during penetration, portal sleeve and penetrating member distal ends 30 and 94 can remain substantially aligned to ease penetration. This is illustrated in FIG. 2 where phantom lines represent the original positions of the portal sleeve and penetrating member prior to penetrating into the anatomical cavity wall and the solid lines represent their positions during penetration.

As the portal sleeve flange 32 moves proximally, the operating member formed thereby engages leg 88 to pivot trigger 82 clockwise, looking at FIG. 2, to allow the operating member to pass thereby. The clockwise pivotal movement of trigger 82 does not cause movement of the latch 76 since there is no engagement by either leg 86 or 88 with arm extension 80. Once the operating member passes by leg 88, a torsion spring of the leg returns trigger 82 to its normal position with leg 86 adjacent arm extension 80. Accordingly, during penetration of the anatomical cavity wall, no force is required to overcome the bias of extending member 48.

Once the distal end 30 of the portal sleeve 26 has passed through the cavity wall, a reduction in the force from tissue contact on the distal ends of the portal sleeve and penetrating member will cause the portal sleeve and penetrating member to move distally under the bias of bias members 44 and 49, respectively. As the portal sleeve 26 moves distally, flange 32 engages leg 88 of trigger 82 causing the trigger to pivot counterclockwise looking at FIG. 3 and causing leg 86 to engage arm extension 80 moving arm 74 toward base 68 against the force of spring strip 66. The movement of arm 74 away from the longitudinal axis of the safety penetrating instrument causes latch 76 to move out of engagement with the rail member forward wall 38 thereby allowing extending member 48 to move the portal sleeve further distally to the extended protruding position where distal end 30 protrudes beyond the distal tip 96 of the penetrating member as illustrated in FIG. 3, thereby protecting tissue within the anatomical cavity from inadvertent contact with the distal tip 96. With the distal end 30 of portal sleeve 26 in the anatomical cavity, the penetrating unit 24 can be withdrawn from the portal unit 22 leaving the portal sleeve in place such that instruments for performing endoscopic procedures can be introduced into the cavity via the portal formed by the portal unit 22.

Figure 4:
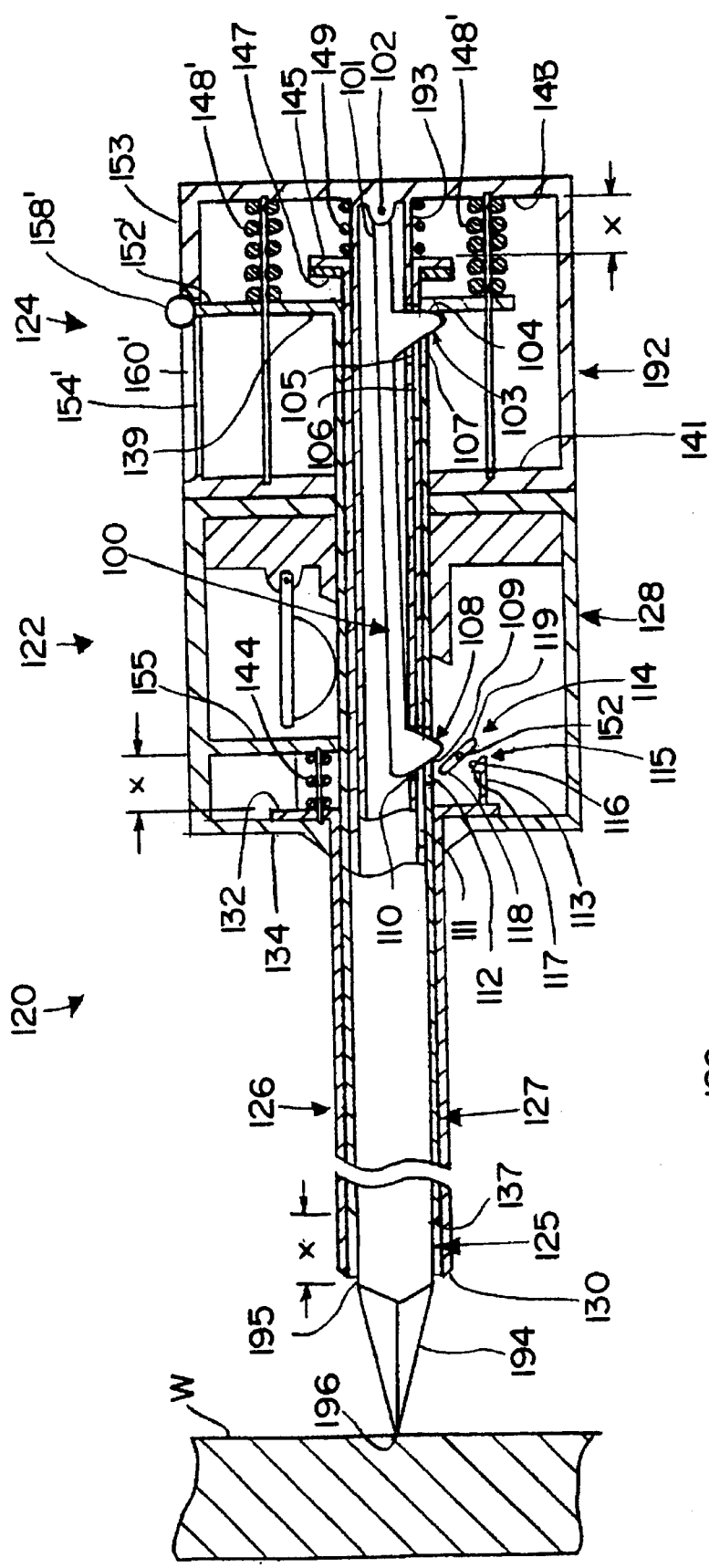
FIG. 4 is a broken side view, partly in section, of a modification of a safety penetrating instrument according to the present invention.

A modification of the safety penetrating instrument according to the present invention is shown at 120 in FIG. 4. The modified safety penetrating instrument 120 is similar to safety penetrating instrument 20 except that movement of a safety shield to an extended protruding position is triggered by distally-biased movement of the portal sleeve in response to a reduction in the force from tissue contact following entry into the anatomical cavity. Safety penetrating instrument 120 includes a portal unit 122 and a penetrating unit 124. The penetrating unit 124 includes a penetrating member 125, a safety shield 127 and a hub 192 mounting proximal ends of the penetrating member and safety shield. Safety shield 127 is generally tubular and is disposed between the penetrating member 125 and portal sleeve 126 when hub 192 is mated with housing 128. The safety shield 127 terminates distally at a distal end 137 and proximally at a transverse flange or plate 139 disposed between forward and rear walls 141 and 143 of the hub 192. Flange 139 extends toward an upper wall 153 of the hub and carries a pin 152', similar to pin 52, while passing through a longitudinal slot 154' in the hub upper wall to terminate at a handle 158' disposed within a longitudinal groove or recess 160'. Penetrating member 125 is at least partly hollow and is telescopically fitted over guide tube 193. Proximal flange 145 of the penetrating member is disposed between an inner wall 147 oriented perpendicular to the longitudinal axis of the hub and hub rear wall 143. Bias member 149 is similar to bias member 49 and is disposed around guide tube 193 and held in compression between the penetrating member flange 145 and the rear wall 143 of the hub. Extending members 148', each similar to extending member 48, are held in compression between safety shield flange 139 and hub rear wall 143.

Safety shield flange 139 is locked in the retracted position shown in FIG. 4 by a longitudinal latch arm 100 disposed within the guide tube 193 and having a proximal end 101 pivotally mounted on a pin 102 secured to the rear wall 143 of the hub. A torsion spring or the like (not shown) is connected between the pin 102 and latch arm 100 or between the guide tube inner wall and latch arm 100 to bias the arm 100 in a counterclockwise direction looking at FIG. 4. Latch arm 100 carries a latching protrusion 103 with a transverse latching surface 104 configured to extend through aligned slots 105, 106 and 107 formed in the guide tube, penetrating member and safety shield to engage safety shield flange 139. Slot 106 formed in the penetrating member 125 is sufficiently long to allow movement of the penetrating member between inner and rear walls of the hub. A triggering protrusion 108 is formed at a distal end of the latch arm 100 and includes a curved distal edge 109 that protrudes through aligned slots 110, 111 and 112 formed in the guide tube 193, penetrating member 125 and safety shield 127 distally of slots 105, 106 and 107 to communicate into housing 128.

Portal unit 122 is similar to portal unit 22 for safety penetrating instrument 20 but with the portal sleeve flange 132 mounted between the housing front wall 134 and an inner wall 155 extending perpendicular to the longitudinal axis of the instrument. Additionally, a finger 113 extends perpendicularly from the portal sleeve flange 132 in a proximal direction and a lever 114 is disposed between the finger 113 and triggering protrusion 108. Finger 113 terminates proximally in a barb 115 with an acutely angled leading edge 116 and a vertical trailing edge 117 parallel to flange 132. Lever 114 is pivotally mounted on a pin 152 secured to a wall or walls of housing 128 perpendicular to the longitudinal axis of the penetrating instrument, and includes axially opposed ends 118 and 119. Finger 113 is positioned on flange 132 in a manner to engage lower end 119 of lever 114 when moved proximally. Upper end 118 of lever 114 is rotatable in a clockwise direction to contact triggering protrusion 108.

Figure 5:
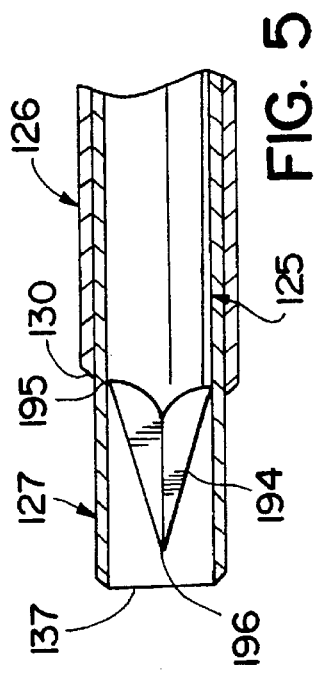
FIG. 5 is a fragmentary side view, partly in section, of a distal end of the safety penetrating instrument of FIG. 4 following penetration into the anatomical cavity.

Use of the safety penetrating instrument 120 is similar to that described above with respect to safety penetrating instrument 20 in that, when the user desires to penetrate into an anatomical cavity, the safety penetrating instrument will normally be provided with the safety shield 127 in the extended position shown in FIG. 5 where the distal end 137 of the safety shield protrudes beyond the penetrating member distal end 194 to protect distal tip 196. Additionally, the portal sleeve 126 will be provided in a rest position where the distal end 130 of the portal sleeve is aligned with the penetrating member distal transition 195 and the portal sleeve flange 132 abuts the housing front wall 134. In the rest position, barb 115 on finger 113 will be disposed distally of lever lower end 119. The safety shield 127 is biased to the extended protruding position by extending member 148' with handle 158' being disposed at a distal end of the slot 154' in hub 192.

Prior to commencing penetration of an anatomical cavity wall, handle 158' is grasped and manually moved proximally to move safety shield 127 proximally against the bias of extending member 148' until safety shield flange 139 rides over latching protrusion 103 by engaging an outwardly angled distal surface of the latching protrusion 103 to move the latch arm 100 clockwise looking at FIG. 4. When safety shield flange 139 moves proximally past latching surface 104, latch arm 100 springs back in a counterclockwise direction to lock the safety shield in the retracted position. The user can feel the safety shield flange lock into place in engagement with latch arm 100 and can also visually determine that the safety shield is in the locked retracted position by noting the position of the handle 158' at a proximal end of the slot 154'. With the safety shield 127 locked in the retracted position, the distal end 137 of the safety shield will be disposed proximally of the transverse dimensional transition 195 of the penetrating member 125 a predetermined distance x approximately equal to the distance between portal sleeve flange 132 and inner wall 155 in housing 28 and the distance between penetrating member flange 145 and the hub rear wall 143, the distal end 130 of the portal sleeve 126 will be disposed adjacent the dimensional transition 195, and portal sleeve flange 132 will remain biased by spring 144 into abutment with housing forward wall 134.

With the safety penetrating instrument 120 in the position illustrated in FIG. 4, penetration of the anatomical cavity wall is commenced, and the force from tissue contact on the portal sleeve and penetrating member distal ends 130 and 194 will cause the portal sleeve and penetrating member to move together proximally against the bias of springs 144 and 149, respectively. Proximal movement of the portal sleeve 126 also causes barb 115 carried by finger 113 to contact and move past lever lower end 119 causing lever 114 to rotate counterclockwise. Lever upper end 118 is thus moved away from triggering protrusion 108 without causing any movement of latch arm 100. Accordingly, the barb 115 will then be positioned proximally of the lever lower end 119. Upon entry into the anatomical cavity, the counter force on the distal end of the portal sleeve will be reduced allowing spring 144 to move the portal sleeve distally causing barb 115 to engage lever lower end 119 and thereby to pivot the lever 114 clockwise causing lever upper end 118 to engage triggering protrusion 108. The engagement of lever 114 with triggering protrusion 108 causes lever arm 100 to rotate clockwise moving the latching protrusion 103 out of engagement with the safety shield flange 139 thereby allowing extending member 148' to cause the safety shield to move distally to the extended protruding position shown in FIG. 5 wherein the safety shield distal end 137 protrudes beyond the distal end 194 of penetrating member 125 to protect the tip 196 of the penetrating member. The penetrating unit 124 can then be withdrawn from the portal unit 122 leaving the portal sleeve 126 in place for the introduction of medical instruments therethrough.

The modified safety penetrating instrument illustrated in FIG. 6 at 220 is similar to safety penetrating instrument 120 with the exception that distally-biased movement of the portal sleeve upon penetrating into an anatomical cavity triggers release of both the safety shield and portal sleeve to move distally from retracted positions exposing the penetrating member distal end to extended protruding positions beyond the penetrating member distal end. The modified safety penetrating instrument 220 includes a penetrating unit 224 similar to penetrating unit 124 for safety penetrating instrument 120 and a portal unit 222 similar to portal unit 22 for safety penetrating instrument 20 but with a finger 213, like finger 113, extending perpendicularly from the portal sleeve flange 232 in a proximal direction and a lever 214, like lever 114, mounted within the housing 228 in a manner to be engaged by finger 213 when the portal sleeve moves and to cam latching protrusion 203 into penetrating member 225 when rotated clockwise looking at FIG. 6.

Operation of the safety penetrating instrument 220 is essentially the same as for safety penetrating instruments 120 and 120 with the exception that handles 258 and 258' coupled with the portal sleeve 226 and safety shield 227, respectively, must be manually moved proximally along slots 254 and 254' in the housing 228 and hub 292, respectively, to position the portal sleeve and safety shield in their respective retracted positions. Portal sleeve flange 232 and the proximally-extending finger 213 carried by the portal sleeve flange function as operating members for triggering release of locking and releasing mechanism 264 holding the portal sleeve and latch arm 200 holding the safety shield to permit the portal sleeve and safety shield to move to extended protruding positions beyond the penetrating member distal end as shown in FIG. 7.

Figure 8:
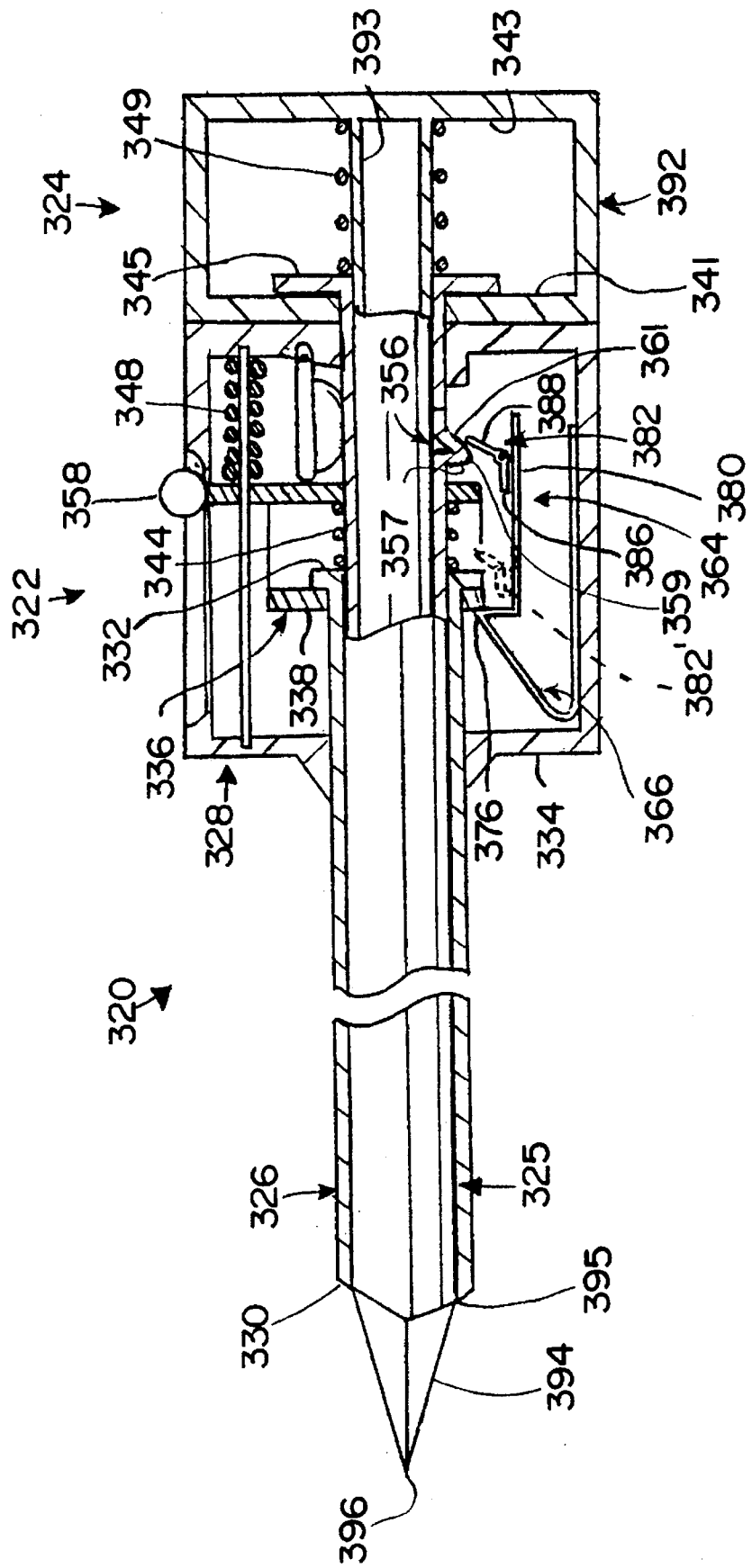
FIG. 8 is a broken side view, partly in section, of a further modification of a safety penetrating instrument according to the present invention.

The safety penetrating instrument 320 illustrated in FIG. 8 is similar to safety penetrating instrument 20 with the exception that movement of the portal sleeve to the extended protruding position is triggered by distally-biased movement of the penetrating member in response to reduction in the force from tissue contact following entry into the anatomical cavity. Penetrating member 325 is similar to penetrating member 25 but carries a radial protrusion 356 suitably positioned to be disposed within housing 328 when hub 392 is mated with housing 328. Radial protrusion 356 can be a separate member carried on or within the penetrating member in a manner to protrude radially therefrom or can be integrally formed as part of the penetrating member as shown. The integral protrusion 356 shown is formed from a tongue of material cut from the tubular body of the penetrating member and is configured to present a transverse distal abutment surface 357 substantially perpendicular to the longitudinal axis of the safety penetrating instrument. A bend 359 joins the transverse distal abutment surface with an acutely angled proximal abutment surface 361.

Locking and releasing mechanism 364 for safety penetrating instrument 320 is the same as locking and releasing mechanism 64 except that trigger 382 is suitable positioned for being engaged by protrusion 356 rather than by the portal sleeve flange 332. As a result, trigger 382 is proximally spaced from flange 332 when the portal sleeve 326 is in the retracted position shown in FIG. 8.

Use of the safety penetrating instrument 320 is similar to that described above for safety penetrating instrument 20 with the exception that penetrating member protrusion 356 rather than portal sleeve flange 332 serves as the operating member for engaging the trigger 382. Prior to penetration, the portal sleeve and penetrating member are in the position shown in FIG. 8 with the penetrating member protrusion 356 located distally of trigger leg 388. During penetration, the portal sleeve and penetrating member are moved proximally due to the force from tissue contact on the portal sleeve and penetrating member distal ends and the penetrating member protrusion 356 is moved proximally with the penetrating member passed trigger leg 388 causing trigger 382 to rotate clockwise looking at FIG. 8. Clockwise rotation of the trigger 382 moves trigger leg 386 away from extension 380 and thus does not release latch 376 holding rail member forward wall 338. Upon penetration into an anatomical cavity, the counter force on the distal end of the penetrating member will be reduced allowing spring 349 to move the penetrating member distally causing the vertical abutment surface 357 of the penetrating member protrusion 356 to engage trigger leg 388, rotating the trigger 382 counterclockwise. Counterclockwise rotation of trigger 382 causes leg 386 to bear against extension 380 moving latch 376 away from rail member forward wall 338 to release the rail member, thereby allowing extending member 348 to move the rail member and the portal sleeve carried therein distally from the retracted position to an extended protruding position beyond the penetrating member distal tip 396 as shown previously in FIG. 3.

Another modification of the safety penetrating instrument of the present invention is arrived at by combining the locking and releasing mechanisms of safety penetrating instruments 20 and 320 to permit movement of the portal sleeve to the extended protruding position in response to distally biased movement of either or both of the portal sleeve and penetrating member. The modification involves mounting a second trigger, shown in phantom at 382' in FIG. 8, distally spaced from trigger 382 for being engaged by portal sleeve flange 332. With two triggers having legs overlying extension 380, it will be appreciated that the counterclockwise rotation of either trigger will result in latch 376 being moved away from rail member 336 to release the rail member and portal sleeve thereby allowing extending member 348 to move the portal sleeve distally to the extended protruding position in response to distally-biased movement of either the portal sleeve or the penetrating member.

Figure 9:
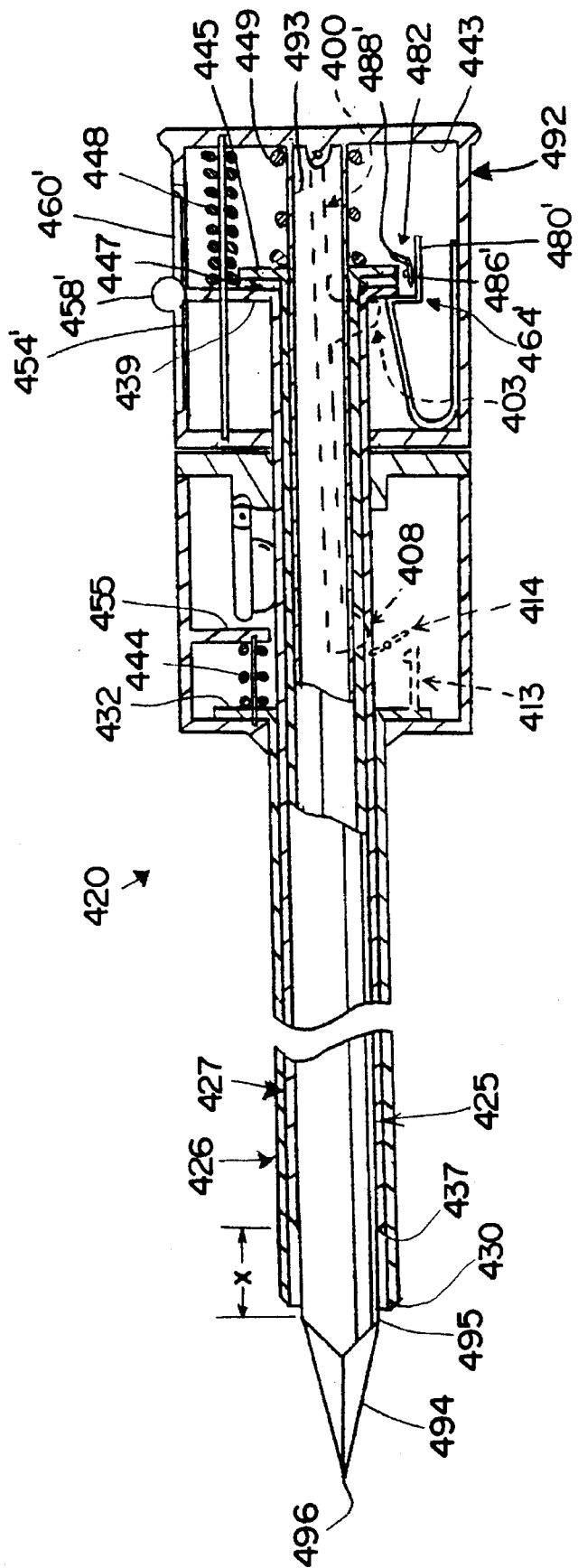
FIG. 9 is a broken side view, partly in section, of another modification of the safety penetrating instrument of the present invention.

Yet another modification of the safety penetrating instrument of the present invention is shown in FIG. 9 wherein the modified safety penetrating instrument 420 is similar to safety penetrating instrument 120 with the exception of the safety shield being triggered to move distally from the retracted position exposing the penetrating member distal end to the extended protruding position beyond the distal end of the penetrating member in response to distally-biased movement of the penetrating member upon penetrating into an anatomical cavity. Safety shield flange 439 is held by a locking and releasing mechanism 464' similar to locking and releasing mechanism 64 but mounted within hub 492. A trigger 482' of locking and releasing mechanism 464' is similar to trigger 82 and is mounted in the hub with a lower leg 486' overlying extension 480' of latch 476 and an upper leg 488' proximally spaced from penetrating member flange 445 when the penetrating member is in a rest position with the penetrating member flange 445 abutting the hub inner wall 447.

Operation of the safety penetrating instrument 420 is essentially the same as for safety penetrating instrument 120 with the exception that the penetrating member flange 445 functions as the operating member for triggering release of locking and releasing mechanism 464' holding the safety shield 427. Portal sleeve and penetrating member distal ends 430 and 494 are distally spaced from safety shield distal end 437 a distance x when the safety shield is retracted and the portal sleeve and penetrating member are in their rest positions as shown. The portal sleeve and penetrating member move together during penetration into alignment with the safety shield to ease penetration. After penetration the safety shield is extended as shown previously in FIG. 5.

Safety penetrating instrument 420 can also be modified as shown in FIG. 9 by mounting a latch arm, shown in phantom at 400, for engaging the safety shield flange 439 in hub 492 and mounting a finger, shown in phantom at 413, on portal sleeve flange 432 for engaging a lever, shown in phantom at 414, for releasing arm 400.

Figure 10:
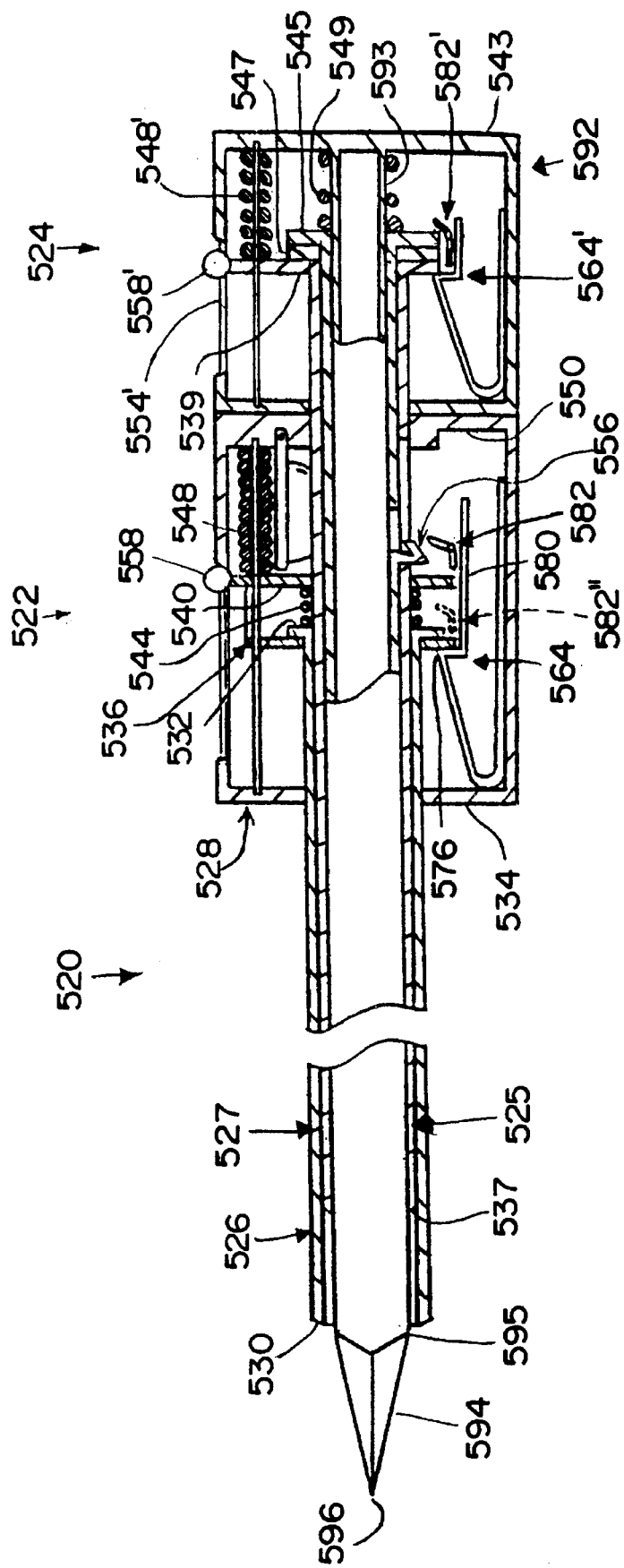
FIG. 10 is a side view, partly in section, of still another modification of the safety penetrating instrument of the present invention.

Yet another modification of the safety penetrating instrument of the present invention is illustrated in FIG. 10 wherein the modified safety penetrating instrument 520 is similar to safety penetrating instrument 420 with the exception that both the portal sleeve and safety shield are triggered to move distally from retracted positions exposing the penetrating member distal end to extended protruding positions beyond the distal tip of the penetrating member in response to distally-biased movement of the penetrating member upon penetrating into an anatomical cavity. Safety penetrating instrument 520 includes a portal unit 522 similar to portal unit 322 for safety penetrating instrument 320 and a penetrating unit 524 similar to penetrating unit 424 for safety penetrating instrument 420. Additionally, penetrating member 525 includes a radial protrusion 556 like radial protrusion 356 for safety penetrating instrument 320.

Locking and releasing mechanism 564 for safety penetrating instrument 520 is mounted within housing 528 for engaging the portal sleeve rail member 536, and a similar locking and releasing mechanism 564' is mounted within the hub 592 for engaging the safety shield flange 539. A pair of extending members 548 and 548' are held in compression between portal sleeve rail member rearward wall 540 and safety shield flange 539 and the rear walls 550 and 543 of the housing and hub, respectively. Bias members 544 and 549 for the portal sleeve and penetrating member are mounted between respective proximal flanges of the portal sleeve and penetrating member and the rail member and hub rear walls allowing both the portal sleeve and penetrating member to move proximally during penetration; however, it is distally-biased movement of the penetrating member that causes protrusion 556 and penetrating member flange 545 to engage triggers 582 and 582' thereby releasing portal sleeve 526 and safety shield 527 to be moved distally to extended positions.

Use of the safety penetrating instrument 520 proceeds essentially in the same manner as previously described with the exception that both the portal sleeve and safety shield must be retracted prior to use in order to expose the penetrating member distal end. Handles 558 and 558' are coupled with the portal sleeve and safety shield, respectively, for this purpose and can be grasped and moved proximally together or individually to move the portal sleeve and safety shield from their extended positions to the retracted positions shown in FIG. 10. Once safety shield and portal sleeve rail members have been locked, penetration of the anatomical cavity wall can be commenced as described previously but with penetrating member protrusion 556 and penetrating member flange 545 serving as operating members.

Another modification of the safety penetrating instrument of the present invention is arrived at by combining the locking and releasing mechanisms of safety penetrating instruments 20 and 520 to permit movement of the portal sleeve to the extended protruding position in response to distally-biased movement of either or both of the portal sleeve and penetrating member. The modification involves mounting a second trigger in the housing, shown in phantom at 582" in FIG. 10, distally spaced from trigger 582 for being engaged by portal sleeve flange 532. With two triggers having legs overlying extension 580, it will be appreciated the counterclockwise rotation of either trigger will result in latch 576 being moved away from rail member 536 to release the rail member and portal sleeve thereby allowing extending member 548 to move the portal sleeve distally to the extended protruding position, shown previously in FIG. 7, in response to distally-biased movement of either the portal sleeve or the penetrating member.

In the embodiments shown, the distal end of the cannula is aligned with a transverse dimensional transition along the longitudinal axis of the penetrating member at the penetrating member distal end immediately prior to use of the safety penetrating instrument for penetrating the anatomical cavity wall; and since both the portal sleeve and penetrating member are movable during penetration, the distal ends of the portal sleeve and penetrating member are generally aligned during penetration, with one or both of the portal sleeve and penetrating member triggering protrusion of a safety member when moving distally toward the original rest position upon entering the anatomical cavity.

Figure 11:
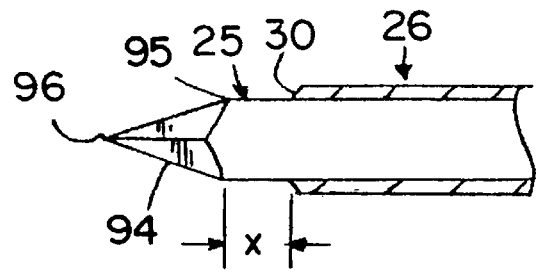
FIGS. 11–13 are side views, partly in section, of alternative distal configurations for the safety penetrating instrument of the present invention prior to penetrating into an anatomical cavity wall.

FIG. 11 shows an alternative distal configuration for the safety penetrating instruments of the present invention wherein the portal sleeve distal end 30 is located proximally of the penetrating member distal end transition 95 prior to use. In this configuration the portal sleeve will begin to move further proximally only after the penetrating member 25 has proximally moved a predetermined distance X (i.e., by advancing through the anatomical cavity wall and retracting within hub 92) and will spring back to its original position proximal of the penetrating member distal end transition 98 when both members enter into the anatomical cavity thereby triggering protrusion of the portal sleeve (and/or safety shield if provided) beyond the penetrating member distal end 94 to function as a safety member.

Figure 12:
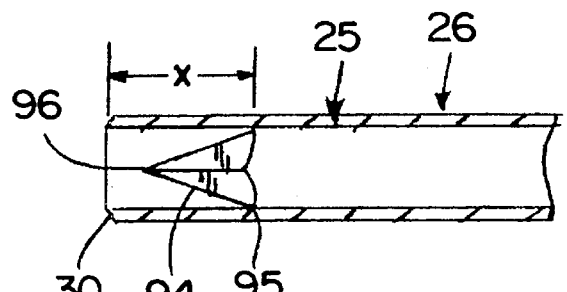

Another distal configuration for the safety penetrating instruments of the present invention is shown in FIG. 12 wherein the distal end 30 of the portal sleeve is spaced distally of the penetrating member distal end transition 95 a predetermined distance X. In this configuration the portal sleeve will move proximally during penetration towards becoming aligned with the distal end transition of the penetrating member and will move together with the penetrating member to ease penetration by providing a smooth profile. The portal sleeve and penetrating member will spring back to their original positions upon entering into the anatomical cavity thereby triggering further distal movement or protrusion beyond the penetrating member distal end by the portal sleeve (and/or the safety shield if provided).

Figure 13:
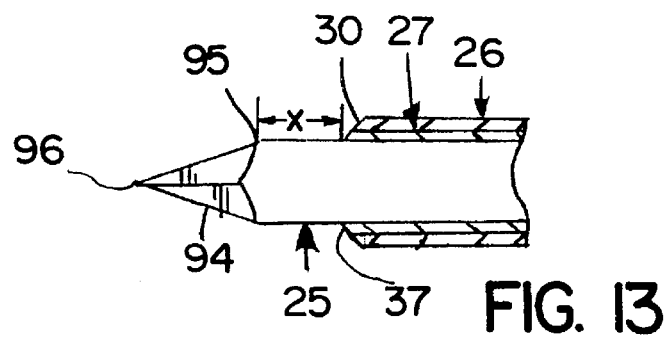

FIG. 13 shows an alternative distal configuration for the safety penetrating instruments of the present invention wherein the distal ends 30 and 37 of the portal sleeve 26 and safety shield 27 are spaced distally from the penetrating member distal end transition 95 prior to use a predetermined distance X. In this configuration the penetrating member distal end 94 will move proximally during penetration towards becoming aligned with the portal sleeve and safety shield distal ends 30 and 37 and will stop prior to or when it reaches the safety shield distal end 37 at which point the portal sleeve 26 will begin to move proximally away from the safety shield distal end 37. The portal sleeve 26 and penetrating member 25 will spring back towards their original rest positions upon entering into the anatomical cavity thereby triggering protrusion beyond the penetrating member distal end 94 by the portal sleeve and/or the safety shield.

From the above, it will be appreciated that the portal sleeve and penetrating member of the safety penetrating instrument of the present invention are movable proximally during penetration of an anatomical cavity wall and distally upon entering the anatomical cavity to trigger further distal movement or protrusion of the portal sleeve and/or the safety shield or probe to function as safety members protecting the distal end of the penetrating member. By "safety member" is meant any structure moveable distally relative to the penetrating member to protect the tip of the penetrating member within an anatomical cavity. Since in the safety penetrating instrument of the present invention one or both of the portal sleeve and safety shield can be extended to protect the penetrating member tip, each can function as a safety member upon penetration of the safety penetrating instrument into an anatomical cavity. The cannula, whether or not it functions as a safety member, can be a portal sleeve, a needle open at both ends with fluid flow therethrough, a catheter or any other tubular component of a medical instrument. When the cannula is not triggered to protrude as a safety member, it is coupled with a safety member such as a tubular safety shield disposed between the cannula and a penetrating member, a safety probe fitted within a hollow penetrating member, or a component partly within and around the penetrating member and movable distally to protrude relative to the penetrating member to protect the distal end thereof when triggered. On the other hand, if the cannula does function as a safety member, it can be coupled with a protective sheath or probe that is not triggered to protrude or with any of the aforementioned safety members. Redundant safety can also be achieved by biasing the safety shield and/or penetrating member distally while allowing one or both to move proximally during penetration and triggering release of the safety member in response to distal movement of one or more of the cannula, the safety shield and the penetrating member upon entry into the anatomical cavity. Additionally, the triggered safety member protrusion can be combined with penetrating member retraction to provide separate modes of safety.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal ends of the cannula and the safety shield can be chamfered or blunt, smooth or roughened, or have any other configuration depending on the need for ease of penetration or increased resistance. Further, the safety shield can be mounted either by the portal unit or the penetrating unit depending on the desirability of being left in place within the portal sleeve or withdrawn with the penetrating member.

Figure 14:
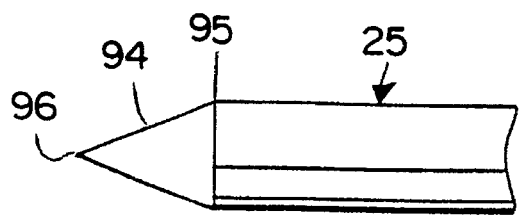
FIGS. 14–19 are side views of alternative distal configurations for the penetrating member of the safety penetrating instrument of the present invention.
Figure 15:
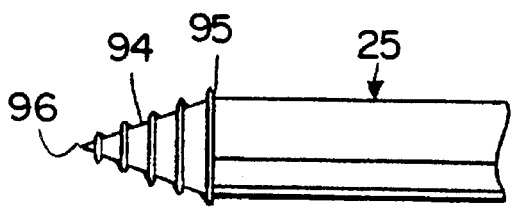
Figure 16:
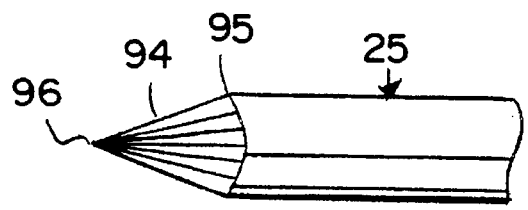
Figure 17:
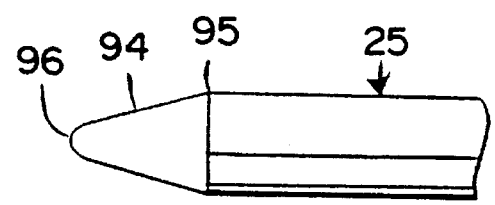
Figure 18:
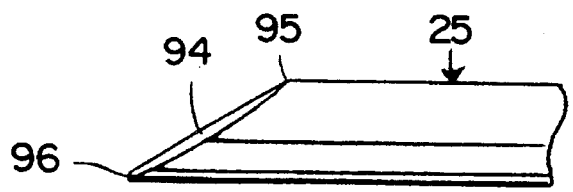
Figure 19:
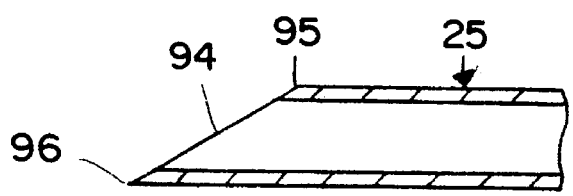

The penetrating member can be solid, hollow or partially solid and hollow, formed as single or multiple pieces, and fixed as shown or movable telescopically over a guide tube or the like. The distal end 94 of the penetrating member 25 can have any configuration desired for a particular procedure, for example, the pyramidal trocar configuration shown or a conical distal end (FIG. 14), a threaded distal end (FIG. 15), a multifaceted distal end (i.e., having two or more facets as shown in FIG. 16), a blunt distal end (FIG. 17), a slanted distal end (FIG. 18) or a hollow needle configuration with fluid flow therethrough (FIG. 19). Additionally, the surface defining the distal end of the penetrating member can be irregular or smooth, continuous or perforated, provided with cutting features or having any combination of the above. If the penetrating member 25 is a hollow needle having a beveled end 94 as shown or a curved Tuohey-type distal configuration, the proximal edge of the opening at the distal end of the needle is considered the transverse dimensional transition 95 and thus the cannula and/or safety shield distal end is aligned with the distal end of the needle when located adjacent the proximal edge 95.

Figure 20:
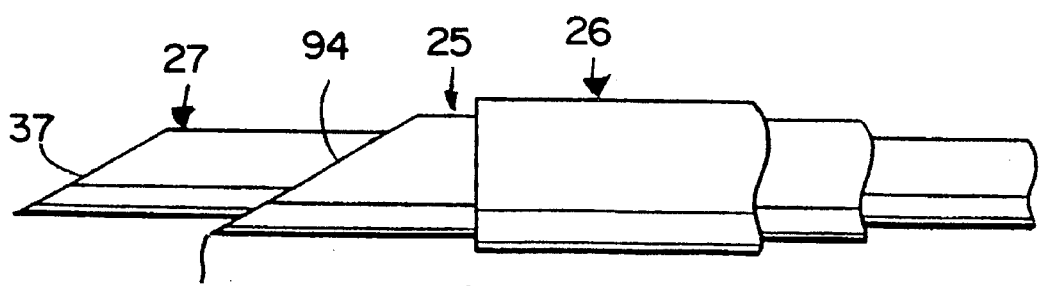
FIG. 20 is a side view, partly in section, of the distal end of a penetrating member configured to accommodate a safety probe.

As mentioned previously, the safety member of the present invention can be a tubular member such as the cannula or a safety shield disposed between the cannula and penetrating member, or in the case of a hollow penetrating member, the safety member can be a probe disposed at least partially within the penetrating member and movable through one or more apertures formed at or near the distal end of the penetrating member. FIG. 20 shows a cannula 26 surrounding a hollow penetrating member 25 with a beveled distal opening 94 and a cylindrical safety probe 27 in an extended protruding position to protect the distal end of the penetrating member. The safety probe has a beveled distal end 37 with a blunt tip and is preferably movable from the extended position shown to a retracted position where the beveled distal end 37 of the safety probe is flush with the distal end 94 of the penetrating member. It will be appreciated that a coaxial extending mechanism can be fitted within the penetrating member to move the safety probe to the extended position or a flange can be carried at the safety probe proximal end and passed through a slot or opening in the penetrating member to be acted on by any of the extending mechanisms previously described. The safety probe distal end can have any configuration to protrude through single or multiple openings formed in the penetrating member distal end and can conform to the distal profile of the penetrating member or present a discontinuous surface when retracted.

The rail members can have various configurations to engage the latch and be released by the trigger. Preferably, the rail member will have a configuration to serve as a stop or abutment for the operating member as exemplified herein by a U-shaped rail member.

The locking and releasing mechanisms require only a latch for locking the safety member in the retracted position and a trigger for releasing the latch in response to distal movement of an operating member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in Applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1992, Ser. No. 07/929,338, filed Aug. 14, 1992, Ser. No. 07/845,177, filed Sep. 15, 1992, Ser. No. 07,945, 177, filed Sep. 15, 1992, Ser. No. 08/079,586, filed Jun. 22, 1993, Ser. No. 08/195,512, filed Feb. 14, 1994, Ser. No. 08/196,029, filed Feb. 14, 1994, Ser. No. 08/196,027, filed Feb. 14, 1994, Ser. No. 08/195,178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference. The above applications disclose automatically retracting safety penetrating instruments such that modification of the locking and releasing mechanisms requires configuring the latches to lock a member in a retracted position rather than in an extended position. The above applications also disclose various bias arrangements useful with the safety penetrating instrument of the present invention. Other locking and releasing mechanisms that can be used in the safety penetrating instrument of the present invention are disclosed in Applicant's pending applications Ser. Nos. 08/279,170 and 08/279,172, filed Jul. 22, 1994, the disclosures of which are incorporated herein by reference.

One or more control buttons, such as the control buttons described in Applicant's copending patent application Ser. No. 08/083,220, filed Jun. 24, 1993, can be mounted next to any latch for manually disengaging the latch to prevent locking of the safety member in the retracted position, in some cases converting the safety penetrating instrument to a standard safety shielded penetrating instrument without triggered protrusion. In addition, any latch can carry a secondary pawl or protrusion at a distal end for locking the safety member in the extended position and can then be released through the use of a control button as described above.

The transverse or radial protrusions 356 and 556 carried by the penetrating member can be integrally formed on an exterior surface of the penetrating member as shown or can be mounted within the penetrating member as part of a pivoted lever protruding through slots in the penetrating member and safety shield to engage the triggers in their respective housings. If part of a pivoted lever, the protrusions can be made to withdraw into their respective safety shields by rotating the lever, for example by use of a control button positioned adjacent the lever and operable to cam the lever in a manner to withdraw the protrusion.

It will also be appreciated that the safety penetrating instrument of the present invention permits use of strong bias springs to ensure movement of the safety member (whether it be the cannula, a safety shield or probe, or both) to the extended protruding position without increasing the force to penetrate. After penetration of the safety penetrating instrument into the anatomical cavity, the safety member acts as a shock absorber upon inadvertent contact with tissue which contact can be felt by the surgeon and visually determined by movement of the handle. The distal bias for the triggering member (i.e., the cannula and/or penetrating member) of the safety penetrating instrument need only be strong enough to allow slight movement of the member during penetration such that the force-to-penetrate can be minimized. The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall, said penetrating member being movable relative to said housing between an extended rest position and a penetrating member retracted position relative to said cannula;

cannula extending means for moving said cannula distally relative to said housing from a cannula retracted position where said cannula distal end is disposed proximally of said penetrating member distal end to an extended position where said cannula distal end protrudes distally from said penetrating member distal end means for manually moving said cannula proximally relative to said housing from said cannula extended position to said cannula retracted position;

cannula locking means for locking said cannula in said cannula retracted position to prevent distal movement of said cannula relative to said housing beyond said cannula retracted position while permitting proximal movement of said cannula relative to said housing during penetration of the anatomical cavity wall;

cannula bias means for biasing said cannula distally relative to said housing in said cannula retracted position to permit said cannula to move proximally relative to said housing from said cannula retracted position during penetration of the anatomical cavity wall and distally relative to said housing toward said cannula retracted position upon introduction into the anatomical cavity;

penetrating member bias means for biasing said penetrating member distally relative to said housing toward said penetrating member rest position and for permitting proximal movement of said penetrating member relative to said housing; and releasing means responsive to penetration of said safety penetrating instrument into the anatomical cavity for triggering release of said cannula locking means to permit said cannula extending means to move said cannula distally relative to said housing from said cannula retracted position to said cannula extended position.

2. A safety penetrating instrument as recited in claim 1 wherein said releasing means is responsive to distally-biased movement of said cannula upon penetrating into the anatomical cavity.

3. A safety penetrating instrument as recited in claim 1 wherein said releasing means is responsive to distally-biased movement of said penetrating member upon penetrating into the anatomical cavity.

4. A safety penetrating instrument as recited in claim 1 wherein said releasing means is responsive to distally-biased movement of said cannula and said penetrating member upon penetrating into the anatomical cavity.

5. A safety penetrating instrument as recited in claim 1 and further comprising a safety member including a tubular safety shield disposed between said penetrating member and said cannula.

6. A safety penetrating instrument as recited in claim 1 wherein said penetrating member is at least partly hollow and further comprising a safety member including a safety probe disposed within said penetrating member.

7. A safety penetrating instrument as recited in claim 1 wherein said penetrating member distal end extends distally from a transverse dimensional transition in said penetrating member and said cannula distal end is aligned with said transition when in said retracted position.

8. A safety penetrating instrument as recited in claim 1 wherein said penetrating member distal end extends distally from a transverse dimensional transition in said penetrating member and said cannula distal end is located proximally of said transition when in said retracted position.

9. A safety penetrating instrument for establishing a portal in the wall of an anatomical cavity comprising an elongate cannula having a distal end for introduction in the anatomical cavity and a proximal end for positioning externally of the anatomical cavity:

a penetrating member disposed in said cannula and having a distal end for penetrating the anatomical cavity wall, said penetrating member being movable between an extended rest position and a penetrating member retracted position relative to said cannula;

cannula extending mean for moving said cannula to an extended position where said cannula distal end protrudes distally from said penetrating member distal end and for permitting said cannula to move proximally to a retracted position where said cannula distal end is disposed proximally of said penetrating member distal end to expose said penetrating member;

means for manually moving said cannula from said cannula extended position to said cannula retracted position;

cannula locking means for locking said cannula in said cannula retracted position to prevent distal movement of said cannula beyond said cannula retracted position while permitting proximal movement of said cannula during penetration of the anatomical cavity wall;

cannula bias means for biasing said cannula distally in said cannula retracted position to permit said cannula to move proximally from said cannula retracted position during penetration of the anatomical cavity wall and distally toward said cannula retracted position upon introduction into the anatomical cavity;

penetrating member bias means for biasing said penetrating member distally toward said penetrating member rest position and preventing proximal movement of said penetrating member; and releasing means responsive to penetration of said safety penetrating instrument into the anatomical cavity for triggering release of said cannula locking means to permit said cannula extending means to move said cannula to said cannula extended position;

wherein said penetrating member distal end extends distally from a transverse dimensional transition in said penetrating member and said cannula distal end is located distally of said transition when in said retracted position.

10. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall;

a safety member disposed within said cannula and having a distal end, said safety member being movable relative to said housing between a safety member extended position where said safety member distal end protrudes distally from said penetrating member distal end and a safety member retracted position where said safety member distal end is disposed proximally of said penetrating member distal end to expose said penetrating member distal end;

safety member extending means for moving said safety member distally relative to said housing from said safety member retracted position to said safety member extended position;

means for manually moving said safety member proximally relative to said housing from said safety member extended position to said safety member retracted position;

safety member locking means for locking said safety member in said retracted position to prevent movement of said safety member to said safety member extended position;

cannula bias means for biasing said cannula distally relative to said housing toward a cannula rest position and for permitting proximal movement of said cannula relative to said housing;

penetrating member bias means for biasing said penetrating member distally relative to said housing toward a penetrating member rest position and for permitting proximal movement of said penetrating member relative to said housing; and releasing means responsive to penetration of said safety penetrating instrument into the anatomical cavity for triggering release of said safety member locking means to permit said safety member extending means to move said safety member distally relative to said housing from said safety member retracted position to said safety member extended position.

11. A safety penetrating instrument as recited in claim 10 wherein said releasing means is responsive to distally-biased movement of said cannula upon penetrating into the anatomical cavity.

12. A safety penetrating instrument as recited in claim 10 wherein said releasing means is responsive to distally-biased movement of said penetrating member upon penetrating into the anatomical cavity.

13. A safety penetrating instrument as recited in claim 10 wherein said releasing means is responsive to distally-biased movement of said cannula and said penetrating member upon penetrating into the anatomical cavity.

14. A safety penetrating instrument as recited in claim 10 wherein said safety member is a tubular safety shield disposed between said penetrating member and said cannula.

15. A safety penetrating instrument as recited in claim 10 wherein said penetrating member is at least partly hollow and said safety member is a safety probe disposed within said penetrating member.

16. A safety penetrating instrument as recited in claim 10 wherein said penetrating member distal end extends distally from a transverse dimensional transition in said penetrating member and said safety member distal end is located proximally of said transition when said safety member is in said retracted position and said penetrating member is in said rest position.

17. A safety penetrating instrument as recited in claim 16 wherein said cannula distal end is aligned with said safety member distal end when said cannula is in said rest position and said safety member is in said retracted position.

18. A safety penetrating instrument as recited in claim 16 wherein said cannula distal end is spaced proximally of said safety member distal end when said cannula is in said rest position and said safety member is in said retracted position.

19. A safety penetrating instrument as recited in claim 16 wherein said cannula distal end is spaced distally of said safety member distal end when said cannula is in said rest position and said safety member is in said retracted position.

20. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall;

a safety member disposed within said cannula and having a distal end, said safety member being movable relative to said housing between a safety member extended position where said safety member distal end protrudes distally from said penetrating member distal end and a safety member retracted position where said safety member distal end is disposed proximally of said penetrating member distal end to expose said penetrating member distal end;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

safety member extending means for moving said safety member distally relative to said housing from said safety member retracted position to safety member extended position;

means for manually moving said cannula proximally relative to said housing from said cannula extended position to said cannula retracted position;

means for manually moving said safety member proximally relative to said housing from said safety member extended position to said safety member retracted position;

cannula locking means for locking said cannula in said cannula retracted position to prevent distal movement of said cannula relative to said housing beyond said cannula retracted position while permitting proximal movement of said cannula relative to said housing during penetration of the anatomical cavity wall;

safety member locking means for locking said safety member in said retracted position to prevent movement of said safety member to said safety member extended position during penetration of the anatomical cavity wall;

cannula bias means for biasing said cannula distally relative to said housing in said cannula retracted position to permit said cannula to move proximally relative to said housing from said cannula retracted position during penetration of the anatomical cavity wall and distally relative to said housing toward said cannula retracted position upon introduction into the anatomical cavity;

penetrating member bias means for biasing said penetrating member distally relative to said housing toward an extended rest position and for permitting said penetrating member to move proximally relative to said housing from said penetrating member rest position; and releasing means responsive to penetration of said safety penetrating instrument into the anatomical cavity for triggering release of said safety member and cannula locking means to permit said safety member and cannula extending means to move said safety member and cannula distally relative to said housing from said retracted positions to said extended positions.

21. A safety penetrating instrument as recited in claim 20 wherein said releasing means is responsive to distally-biased movement of said cannula upon penetrating into the anatomical cavity.

22. A safety penetrating instrument as recited in claim 20 wherein said releasing means is responsive to distally-biased movement of said penetrating member upon penetrating into the anatomical cavity.

23. A safety penetrating instrument as recited in claim 20 wherein said releasing means is responsive to distally-biased movement of said cannula and said penetrating member upon penetrating into the anatomical cavity.

24. A safety penetrating instrument as recited in claim 20 wherein said safety member is a tubular safety shield disposed between said penetrating member and said cannula.

25. A safety penetrating instrument as recited in claim 20 wherein said penetrating member is at least partly hollow and said safety member is a safety probe disposed within said penetrating member.

26. A safety penetrating instrument as recited in claim 20 wherein said penetrating member distal end extends distally from a transverse dimensional transition in said penetrating member and said safety member distal end is located proximally of said transition when in said retracted position.

27. A safety penetrating instrument as recited in claim 26 wherein said cannula distal end is aligned with said safety member distal end when said safety member and cannula are retracted.

28. A safety penetrating instrument as recited in claim 26 wherein said cannula distal end is spaced proximally of said safety member distal end when said safety member and cannula are retracted.

29. A safety penetrating instrument as recited in claim 26 wherein said cannula distal end is spaced distally of said safety member distal end when said safety member and cannula are retracted.

\* \* \* \* \*